US010501806B2

(12) United States Patent
Breen

(10) Patent No.: US 10,501,806 B2
(45) Date of Patent: Dec. 10, 2019

(54) CHROMOSOMAL ASSESSMENT TO DIFFERENTIATE HISTIOCYTIC MALIGNANCY FROM LYMPHOMA IN DOGS

(71) Applicants: North Carolina State University, Raleigh, NC (US); Matthew Breen, Raleigh, NC (US)

(72) Inventor: Matthew Breen, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/304,388

(22) PCT Filed: Apr. 15, 2015

(86) PCT No.: PCT/US2015/025916
§ 371 (c)(1),
(2) Date: Oct. 14, 2016

(87) PCT Pub. No.: WO2015/160916
PCT Pub. Date: Oct. 22, 2015

(65) Prior Publication Data
US 2017/0037481 A1 Feb. 9, 2017

Related U.S. Application Data

(60) Provisional application No. 61/979,775, filed on Apr. 15, 2014.

(51) Int. Cl.
*C12Q 1/68* (2018.01)
*C07H 21/04* (2006.01)
*C12Q 1/6886* (2018.01)

(52) U.S. Cl.
CPC ..... *C12Q 1/6886* (2013.01); *C12Q 2600/124* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,251,601 | B1 | 6/2001 | Bao et al. |
| 6,905,823 | B2 | 6/2005 | Kallioniemi et al. |
| 7,930,104 | B2 | 4/2011 | Baker et al. |
| 7,960,110 | B2 | 6/2011 | Bastian et al. |
| 9,090,945 | B2 | 7/2015 | Breen |
| 9,290,814 | B2 | 3/2016 | Giafis et al. |
| 2007/0275403 | A1 | 11/2007 | Morrison et al. |
| 2009/0155805 | A1 | 6/2009 | Zhang et al. |
| 2009/0299640 | A1 | 12/2009 | Ellis et al. |
| 2009/0324596 | A1 | 12/2009 | Kang et al. |
| 2013/0011834 | A1 | 1/2013 | Breen |
| 2013/0210014 | A1 | 8/2013 | Sharman |
| 2016/0289767 | A1 | 10/2016 | Breen |
| 2017/0211150 | A1 | 7/2017 | Breen |

FOREIGN PATENT DOCUMENTS

| | | |
|---|---|---|
| EP | 2 513 340 B1 | 6/2016 |
| WO | WO2002/077197 | 10/2002 |
| WO | WO 2002/100246 | 12/2002 |
| WO | WO 2009/051842 | 4/2009 |
| WO | WO2012/078053 | 6/2012 |
| WO | WO 2012/135125 | 10/2012 |
| WO | WO 2017/210115 | 12/2017 |

OTHER PUBLICATIONS

Thomas et al. (J. of Heredity, Am. Genetic Association, vol. 98, No. 5, pp. 474-484, 2007). (Year: 2007).*
Hedan et al. (BMC Cancer, vol. 11, pp. 1-14, May 26, 2011). (Year: 2011).*
Hedan, Benoit et al.;"Molecular cytogenetic characterization of canine histiocytic sarcoma: A spontaneous model for human histiocytic cancer identifies deletion of tumor suppressor genes and highlights influence of genetic background on tumor behavior." <htttp://biomedcentral.com/1471-2407/11/201> 11:201, 2011.
International Search Report and Written Opinion dated Jul. 2, 2015 from related International Application No. PCT/US2015/025916.
Roode, Sarah Culvar.; "Molecular Characterization of Canine Leukemia—Comparative Value and Clinical Applications," A dissertation submitted tot he Graduate Faculty of North Carolina State University in partial fulfillment of the requirements for the degree of Doctor of Philosophy; Raleigh, North Carolina, 2014.
Angstadt, Andrea Y. et al.; "A genome-wide approach to comparative oncology: high-resolution oligonucleotide aCGH of canine and human osteosarcoma pinpoints shared microaberrations," Cancer Genetics, 2012.
Hedan, Benoit et al.; "Molecular cytogenetic characterization of canine histiocytic sarcoma: A spontaneous model for human histiocytic cancer identifies deletion of tumor suppressor genes and highlights influence of genetic background on tumor behavior," <http://www.biomedcentral.com/1471-2407/11/201> Hedan et al. BMC Cancer 2011, 11:201.
Thomas, Rachael et al.; "Refining tumor-associated aneuploidy through 'genomic recoding' of recurrent DNA copy number aberrations in 150 canine non-Hodgkin lymphomas," Leukemia & Lymphoma, 2011.
Supplementary material for Thomas R, et al.; "Refining tumor-associated aneuploidy through 'genomic recoding' of recurrent DNA copy number aberrations in 150 canine non-Hodgkin lymphomas," Leukemia & Lymphoma, 2011.
Al Mulla et al., "Genetic profiling of stage I and II colorectal cancer may predict metastatic relapse," Modern Pathology. vol. 19, No. 5, pp. 648-658 (2006).
Bowman et al. (Molecular Evaluation of Canine Urothelial Carcinoma and the Cell line Model, NCSU CVM Annual Research Forum Award of Excellence for Poster presentation, Feb. 2013). (Year: 2013).
Breen et al. "An integrated 4249 marker FISH/RH map of the canine genome." BMC genomics 5(1):652004).

(Continued)

*Primary Examiner* — Jeanine A Goldberg
(74) *Attorney, Agent, or Firm* — Jenkins, Wilson, Taylor & Hunt, P.A.

(57) ABSTRACT

This invention relates generally to the discovery of an improved method to differentiate histiocytic malignancy from lymphoma or hemangiosarcoma in dogs.

16 Claims, 5 Drawing Sheets

(56) References Cited

OTHER PUBLICATIONS

Figure 1:
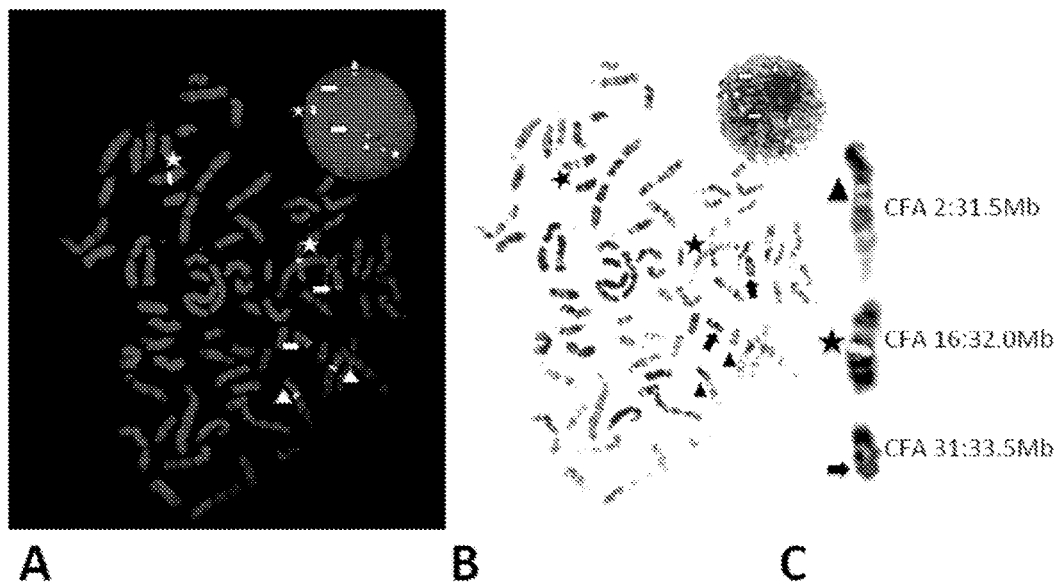

Breen et al. "Chromosome-Specific Single-Locus FISH Probes Allow Anchorage of an 1800-Marker Integrated Radiation-Hybrid/Linkage Map of the Domestic Dog Genome to All Chromosomes", Genome Research, 11:784-1795 (2001).
Breen et al., An integrated 4249 marker FISH/RH map of the canine genome. BMC Genomics, 5:65. (2004).
Breen, M., "Evolutionarily conserved cytogenetic changes in hematological malignancies of dogs and humans—man and his best friend share more than companionship," vol. 16, No. 1, pp. 145-154 (Feb. 25, 2008).
Decision to grant a European patent pursuant to Article 97(1) EPC for European Patent Application No. 10861217.7 dated Jun. 2, 2016.
European Search Report corresponding to European Patent Application No. 10861217.7-1403/2513340 dated Jun. 3, 2013.
Extended European Search Report issued in counterpart European Application No. 14861374.8 dated May 29, 2017 eleven (11) pages).
Hahn et al., "Diagnostic and Prognostic Importance of Chromosomal Aberrations Identified in 61 Dogs with Lymphosarcoma," Veterinary Pathology, vol. 31, No. 5, pp. 528-540 (Sep. 1, 1994).
International Preliminary Report dated Feb. 2, 2017 from related International Application No. PCT/US2015/41988.
International Preliminary Report on Patentability for related PCT Application No. PCT/US2014/065773 dated May 17, 2016.
International search report and the written opinion of the international searching authority for a related PCT Application No. PCT/US2014/065773 dated May 21, 2015.
International Search Report and Written Opinion dated Oct. 30, 2015 from related International Application No. PCT/US2015/41988.
International Search Report and Written Opinion issued in PCT Application No. PCT/US2017/034711 dated Sep. 14, 2017 (six (6) pages).
Karlin-Neumann al. (2012). Probing copy number variations using Bio-Rad's QX100™ Droplet Digital™ PCR system. Bio-Rad Bulletin 6277.
Koenig, A.; "Expression and Significance of p53, Rb, p21/waf-1, p16/ink-4a, and PTEN Tumor Suppressors in Canine Melanoma," Vet Pathol. 39: 458-472 (2002).
Letard S. et al. "Gain-of-Function Mutations in the Extracellular Domain of KIT Are Common in Canine Mast Cell Tumors" Molecular Cancer Research. 2008 pp. 1137-1145 {ten (10) pages).
Lin et al. (Veterinary Immunology and Immunopathology, vol. 127, pp. 114-124, 2009) (Year: 2009).
Lin Tzu-Yin et al., "Targeting canine bladder transitional cell carcinoma with a human bladder cancer-specific ligand", Molecular Cancer, Biomed Central, London, GB, vol. 10, No. 1, Jan. 27, 2011 ( Jan. 27, 2011), age 9, XP02108845 9, ISSN: 1476-4598, DOI: 10.1186/1476-4598-10-9.
Magdy Sayed Aly et al: "Chromosomal aberrations in early-stage bilharzia! bladder cancer", Cancer Genetics and Cytogenetics., vol. 132, No. 1, Jan. 1, 2002 (Jan. 1, 2002), pp. 41-45, XP055372968, us SSN: 0165-4608, DOI: 10. 1016/S0165-4608(01)00527-1.
Maria I. Stamouli et al: "Detection of genetic alterations in primary bladder carcinoma with dual-color and multiplex fluorescence in situ hybridization", Cancer Genetics and Cytogenetics., vol. 149, No. 2, Mar. 1, 004 (Mar. 1, 2004), pp. 107-113, XP055372972, us ISSN: 0165-4608, DOI: 10. 1016/S0165-4608(03)00303-0.
Marin-Aguilera Mercedes et al: "Utility of Fluorescence in Situ Hybridization as a Non-invasive Technique in he Diagnosis of Upper Urinary Tract Urothelial Carcinoma", European Urology, vol. 51, No. 2, Aug. 22, 2006Aug. 22, 2006), pp. 409-415, XP029850986, ISSN: 0302-2838, DOI: 10.1016/J.EURUR0.2006.08.045.
Mochizuki, A. et al. "Detection of Copy Number Imbalance in Canine Urothelial Carcinoma With Droplet Digital Polymerase Chain Reaction" Oncology—Original Article, Veterinary Pathology_ 2016, vol. 53(4) pp. 764-772 (nine (9) pages).

Modiano et al., "Predictive value of p16 or Rb inactivation in a model of naturally occurring canine non Hodgkin's lymphoma," Leukemia. vol. 21, No. 1 pp. 184-187 (2007).
Muller et al. (2012) Genetic characterization via array based comparative genomic hybridization. Tierarztliche Praxis. 40(1):55-58.
Mullins et al. "Agreement in Breast Cancer Classification between Microarray and Quantitative Reverse Transcription PCR from Fresh-Frozen and Formalin-Fixed, Paraffin-Embedded Tissues" Clin Chem. 53(7): 1273-1279 (2007).
Mutsaers, A.J., W.R. Widmer, and D.W. Knapp, Canine transitional cell carcinoma. J Vet Intern Med, 2003. 17(2): p. 136-44.
Notice of Allowance corresponding to Japanese Patent Application No. 2016-554527 dated Feb. 5, 2019.
Notice of Allowance corresponding to U.S. Appl. No. 15/037,438 dated Jun. 7, 2019.
Notification Concerning Transmittal of International Preliminary Report on Patentability (Chapter I of the Patent Cooperation Treaty) corresponding to International Patent Application No. PCT/US2010/060292 dated Aug. 30, 2012.
Notification of Transmittal of the International Search Report and the Written Opinion of the International Searching Authority, or the Declaration corresponding to International Patent Application No. PCT/US2010/060292 dated Apr. 10, 2012.
Office Action correponding to Canadian Patent Application No. 2,785,999 dated Aug. 16, 2016.
Office Action corresponding to Japanese Patent Application No. 2016-554527 dated Sep. 25, 2018. (Translation).
Office Action corresponding to U.S. Appl. No. 13/515,614 dated Jul. 30, 2014.
Office Action corresponding to U.S. Appl. No. 15/037,438 dated Aug. 15, 2017.
Office Action corresponding to U.S. Appl. No. 15/037,438 dated Jan. 8, 2019.
Office Action corresponding to U.S. Appl. No. 15/037,438 dated May 23, 2018.
Office Action corresponding to U.S. Appl. No. 15/037,438 dated Nov. 24, 2017.
Office Action corresponding with European Patent Application No. 10861217.7-1403 dated Apr. 25, 2014.
Office Action corresponding with European Patent Application No. 14861374.8-1118 dated Apr. 4, 2019.
Oral Summons corresponding with European Patent Application No. 10861217.7-1403 dated Jun. 12, 2015.
Ratcliffe et al., "Proteomic identification and profiling of canine lymphoma patients," Veterinary and Comparative Oncology. vol. 7, No. 2 pp. 92-105 (2009).
Sailasuta, A. et al. "The Relevance of CD117-Immunocythochemistry Staining Patterns to Mutational Exon-11 in c-kit Detected by PCR from Fine-Needle Aspirated Canine Mast Cells" Veterinary Medicine International. vol. 2014. pp. 1-8 (eight (8) pages).
Seiser et al. "Reading between the lines: molecular characterization of five widely used canine lymphoid tumour cell lines." Veterinary and comparative oncology 11(1): 30-50 (2013).
Sotirakopolous et al.: "Evaluation of Microsatellite Instability in Urine for the Diagnosis of Transitional Cell Carcinoma of the Lower Urinary Tract in Dogs", J Vet Med, 24: 1445-1451 (2010).
Thomas et al. (Chromosome Research, vol. 10, Apr. 1, 2009 (Year: 2009).
Thomas et al., "A canine cancer-gene microarray for CGH analysis of tumors," Cytogenetic and Genome Research, vol. 102, No. 1-4, pp. 254-260 (2003).
Thomas et al., "A Cytogenetically Characterized, Genome-Anchored 10-M b BAC Set and CGH Array for the Domestic Dog", Journal of Heredity., vol. 98, No. 5, Jul. 23, 2007 (Jul. 23, 2007), pp. 474-484, XP055343142,3B ISSN: 0022-1503, DOI: 10.1093/jhered/esm053.
Thomas et al., "Chromosome aberrations in canine multicentric lymphomas detected with comparative genomic hybridisation and a panel of single locus probes," British Journal of Cancer. vol. 89, No. 8 pp. 1530-1537 (2003).
Thomas, Chromosome Res, vol. 22, No. 3, pp. 305-319, 2017 (Year: 2014).

(56) References Cited

OTHER PUBLICATIONS

Thomas, R., et al. "A genome assembly-integrated dog 1 Mb BAC microarray: a cytogenetic resource for canine cancer studies and comparative genomic analysis." Cytogenetic and genome research 122(2): 110-121 (2008).

Thomas, Rachael et al., "Construction of a 2-Mb resolution BAG microarray for CGH analysis of canine tumors," Genome Research, pp. 1832-1837, Dated Feb. 13, 2005, Revised May 4, 2005.

Urovysion Bladder Cancer Kit; <http://www.abbottmolecular.com> Accessed Nov. 11, 2013.

Urovysion Bladder Cancer Kit; Package Insert; Abbott Laboratories, 2006.

Winkler et al. (2006) Polysomy 13 in a canine prostate carcinoma underlining its significance in the development of prostate cancer. Cancer Genet. Cytogenet. 169:154-158.

\* cited by examiner

AUC
0.89452

CHROMOSOMAL ASSESSMENT TO DIFFERENTIATE HISTIOCYTIC MALIGNANCY FROM LYMPHOMA IN DOGS

CROSS REFERENCE TO RELATED APPLICATIONS

This application is a § 371 U.S. National Stage of International Application PCT/US2015/025916, filed Apr. 15, 2015, which claims the benefit of 61/979,775 filed Apr. 15, 2014, Matthew Breen, entitled "CHROMOSOMAL ASSESSMENT TO DIFFERENTIATE HISTIOCYTIC MALIGNANCY FROM LYMPHOMA IN DOGS", which are hereby incorporated by reference in their entireties.

1. FIELD OF THE INVENTION

This invention relates generally to the discovery of an improved method to differentiate histiocytic malignancy from lymphoma and hemangiosarcoma in dogs.

2. BACKGROUND OF THE INVENTION

2.1. Introduction

It is estimated that there are over 300,000 dogs each year in the United States diagnosed with lymphoma (LSA). Diagnosis of canine lymphoma generally is made following a variety of clinical and pathological assessments, including cytology and/or histopathologic analysis of a tumor biopsy specimen. Untreated cases of canine lymphoma rarely survive beyond three months after diagnosis, but a large proportion (up to 90%) of canine lymphomas are responsive to standard of care (SOC) chemotherapy, using either single agent or multiagent protocols, increasing both the length and quality of an affected dog's life. Median survival with SOC treatment is generally considered to be nine months.

Histiocytic malignancies (HM), frequently reported by pathologists as histiocytic sarcoma, disseminated histiocytic sarcoma, or malignant histiocytosis, are less common in the general dog population, estimated to be diagnosed in fewer than 5,000 cases per year in the US. The incidence of histiocytic neoplasms, however, is remarkably high in some purebred dogs, including the Bernese mountain dog, the flat-coated retriever and the rottweiler. Malignant tumors of histiocytic origin generally have a very poor prognosis (typical survival is just a few weeks post diagnosis) and are considered generally unresponsive to current therapeutic options. For example, in the Bernese mountain dog, 66% of deaths are reported to be due to cancer (BMDCA Health Survey, 2005), of which 47% are attributed to HM, with a further 29% due to lymphoma. These data indicate that ~75% of all cancers and ~50% of all deaths in this breed are due to just these two cancers.

Hemangiosarcomas (HEM) are cancers are tumors of the vascular endothelium, cells that line blood vessels. These cancers represent approx. 2% of all canine cancers and about 5% of all non-cutaneous tumors. Hemangiosarcoma is more common in dogs than any other species and develop primarily in the spleen, heart, or liver. Although usually an indolent disease, hemangiosarcoma is almost always malignant and can spread rapidly. For the affected dog this generally means that the clinical signs may not present until after the tumors have metastasized and/or ruptured. Rupture of a hemangiosarcoma may cause the dog to experience acute shock and collapse. There are clear dog breed predispositions to hemangiosarcoma. Since hemangiosarcoma can affect the same tissues as histiocytic malignancies, pathology is required to provide a confirmed diagnosis.

Fine needle aspiration of a mass may be used to provide cells for cytologic diagnosis, though this has received mixed reviews among pathologists as the cells of a histiocytic malignancy can look very similar to other types of tumors, leading to an inconclusive diagnosis. As such additional tests may need to be performed to obtain a definitive diagnosis. Correct diagnosis of a histiocytic neoplasm currently requires specialized immunohistochemistry (IHC) to distinguish from other neoplasms with similar histological appearances. However, this form of analysis is not always readily available, is time consuming, costly, and requires a particular skill set. In addition, the strong association between key breeds and the incidence of histiocytic malignancy has meant that it is not uncommon for histiocytic malignancy to be provided as the most likely differential, solely due to the breed of the patient, even in the absence of appropriate IHC to provide a robust diagnosis.

The ability to accurately distinguish between canine LSA, HEM, and HM is thus an important goal for the veterinary profession, to ensure most appropriate clinical management of cancer patients. Such an assay would offer considerable value to patient management, adding new approaches to refine diagnosis, and even prognosis.

3. SUMMARY OF THE INVENTION

Described herein, are the foundations for a diagnostic molecular test to separate canine lymphoma and hemangiosarcoma from a histiocytic malignancy. The assay is based on significant differences in the DNA copy number status of selected regions of the canine genome, when evaluating cells obtained from lymphoma, hemangiosarcoma, and histiocytic malignancy tumor samples. There is immediate significance to the veterinary market in being able to readily distinguish these three types of cancer, especially for those breeds that are at high risk of developing these cancers.

Differentiating between histiocytic malignancy and lymphoma: A large cohort of tumor samples pathologically verified as either canine lymphoma or histiocytic malignancy was assembled. Each case was assessed for copy number status (deletion/loss, balanced, gain) of ~180,000 oligonucleotide probes spaced at 13 kb intervals across the canine genome. Suitable aberration calling algorithms were used to define contiguous segments subject to copy number aberration in both cancer types. Statistical comparison of the two datasets revealed regions of the canine genome where the DNA copy number status differed significantly between the two cancer groups. Three of the most significant differences were selected for subsequent assessment, based on segment size. The most significant region, even by itself, offers very high specificity and sensitivity to distinguish between canine lymphoma and a histiocytic malignancy. A multivariate/combined diagnostic model developed from these data offers a highly robust means to separate these two canine cancers. We demonstrated the use of fluorescence in situ hybridization, using probes designed to detect and quantify regions of the canine genome and which are recurrently deleted in histiocytic malignancies, while being either minimally deleted in canine lymphoma, neutral in canine lymphoma, or increased in copy number in canine lymphoma. We further demonstrated the use of digital droplet PCR, using Taq-Man® probes designed in a manner similar to those of the fluorescence in situ hybridization probes in the discrimination of LSA from HM.

The regions of the canine genome where assessment of DNA copy number significantly differentiated canine lymphoma and histiocytic malignancy were subsequently evaluated for their ability to also discriminate between histiocytic malignancy and hemangiosarcoma, using DNA samples isolated from a set of histopathologically verified cases of canine hemangiosarcoma.

Specifically, the disclosure provides a method to differentiate a canine histiocytic malignancy from a lymphoma and from an hemangiosarcoma in a biological sample from a dog which comprises: (a) measuring a copy number of dog chromosome (CFA) 2, CFA 16 and CFA 31 in the biological sample; (b) comparing the measured copy numbers to those of appropriate histiocytic malignancy, hemangiosarcoma and lymphoma controls; and (c) if the copy numbers of CFA 2, CFA 16 and CFA 31 are reduced from that of the appropriate controls, determining that the dog has increased likelihood of presenting with an histiocytic malignancy rather than a lymphoma or an hemangiosarcoma.

The copy number of the regions assessed may be measured by a variety of analytical approaches, including but not limited to the use of fluorescence in situ hybridization (FISH), polymerase chain reaction (PCR), comparative genomic hybridization (CGH), or next generation sequencing.

The biological sample will be representative of the mass and may be a tissue sample such as a tissue biopsy or fine needle aspirate, either intact or presented as a cytological smear, a fresh-frozen sample, a fresh sample, or a formalin-fixed, paraffin-embedded (FFPE) sample.

The disclosure also provides a method of ruling out a dog for a lymphoma treatment wherein the dog may have a histiocytic malignancy or a lymphoma which comprises: (a) measuring a copy number of CFA 2, CFA 16 and CFA 31 in a biological sample from the dog; (b) comparing the measured copy numbers to those of appropriate histiocytic malignancy and lymphoma controls; and (c) if the copy number of CFA 2, CFA 16 and CFA 31 are reduced from that of appropriate controls, identifying the dog as having a histiocytic malignancy and ruling out a lymphoma treatment.

In addition, the disclosure provides a method of identifying a dog with a histiocytic malignancy treatment which comprises (a) measuring a copy number of CFA 2, CFA 16 and CFA 31 in a biological sample from a dog; (b) comparing the measured copy numbers to those of appropriate histiocytic malignancy and lymphoma controls; and (c) if the copy number of CFA 2, CFA 16 and CFA 31 are reduced from that of the appropriate controls, identifying the dog with a histiocytic malignancy.

Also, the disclosure provides a kit for differentiating a histiocytic malignancy from a lymphoma or an hemangiosarcoma in a dog comprising: (a) at least a plurality of reagents selected from the group consisting of: (i) a nucleic acid probe capable of specifically detecting CFA 2, CFA 16 and CFA 31; and (ii) instructions for use in measuring a copy number of CFA 2, CFA 16 and CFA 31 in a biological sample from a dog; (b) wherein if the copy number of CFA 2, CFA 16 and CFA 31 are reduced from that of measured copy numbers for appropriate histiocytic malignancy and lymphoma controls; and (c) determining that the dog has increased likelihood of a histiocytic malignancy rather than a lymphoma or hemangiosarcoma.

4. BRIEF DESCRIPTION OF THE FIGURES

FIG. 1. Validation of FISH probes used to detect and quantify three segments of the canine genome, located on CFA 16 (segment 1), CFA 31 (segment 3) and CFA 2 (segment 4), each of which are subject to highly recurrent copy number loss in histiocytic malignancies but not in canine lymphoma (as per table 1).

Panel A and B all three FISH probes, differentially labeled in (CFA 2, region 4, denoted by a triangle), (CFA 16, region 1, denoted by a star) and (CFA 31, region 3, denoted by an arrow), co-hybridized to a metaphase preparation and interphase nucleus from a healthy dog. In A) the dog chromosomes and nucleus are counterstained in DAPI, while in B) the image has been processed to reveal enhanced DAPI banding of the chromosome. It is clear from panels A and B that that all three probes map to a single location on each pair of homologues of the corresponding dog chromosome, and have two discrete signals in the interphase nucleus shown in the top right of each image.

Panel C one homologue of each of CFA 2, 16 and 31 from panel B, enlarged and correctly oriented to demonstrate more precise chromosomal location of the fluorescence signals. The Mb location (to two decimal places) of the canine genome sequence (reference to CanFam2) represented by each probe is shown to the right of the single homologues.

Figure 2:
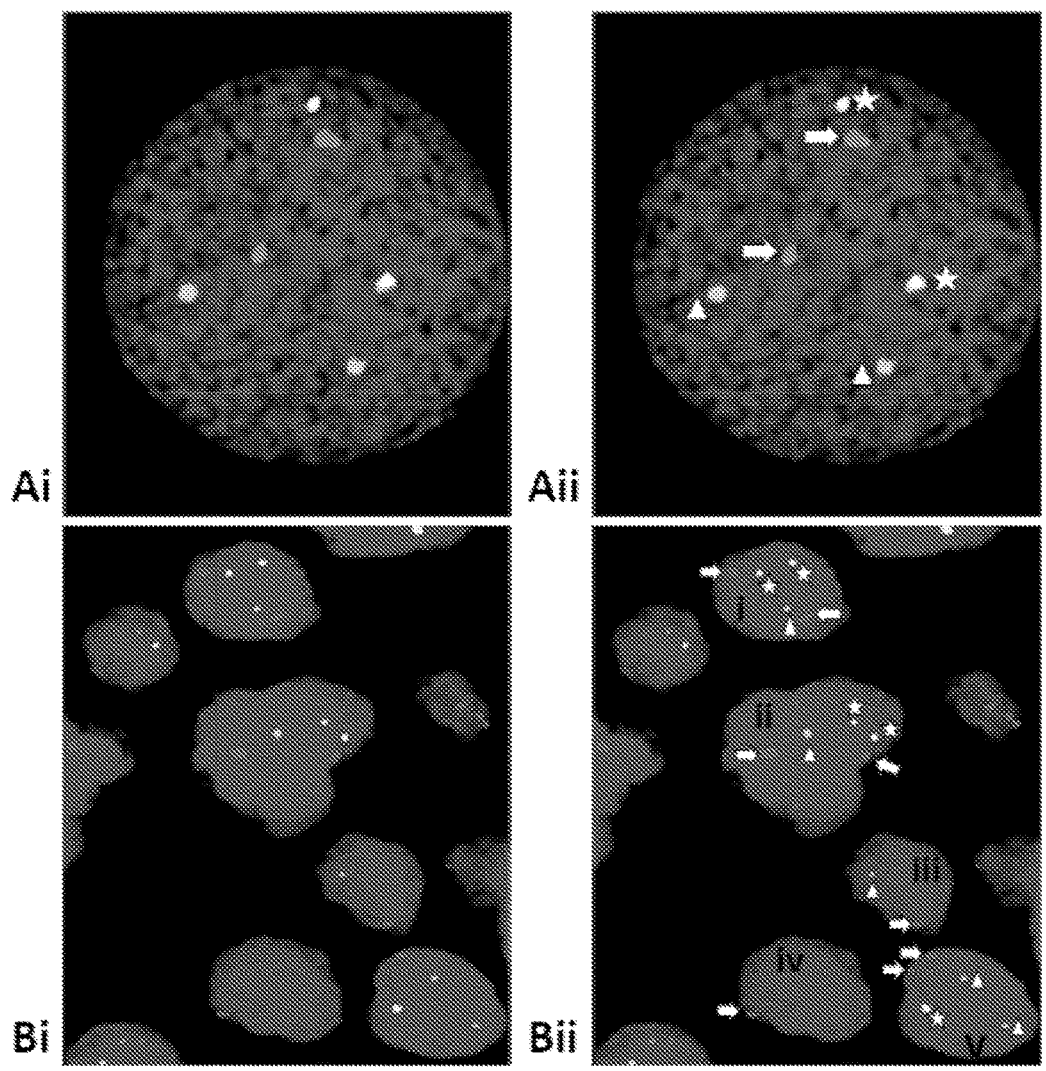

FIG. 2. Use of differential FISH probes to detect and quantify the three target segments of the canine genome from FIG. 1 [CFA 2 (segment 4, denoted by a triangle), CFA 16 (segment 1, denoted by a star) and CFA 31 (segment 3, denoted by an arrow)], which are recurrently subject to copy number loss in histiocytic malignancies and not in canine lymphomas. All three FISH probes are shown co-hybridized to a DAPI stained interphase nucleus from Panel A) a healthy dog and Panel B) group of DAPI stained interphase nuclei from a dog with confirmed histiocytic sarcoma.

Panel A—all three probes are seen as two discrete signals, shown with adjacent symbols (CFA 2=triangle, CFA 16=star, CFA 31=arrow) in Aii. Copy number recording for this cell would be represented as CFA 2=2, CFA 16=2, CFA 31=2. A copy number of n=2 is considered normal for a diploid organism.

Panel B—it is clear that not all signals are present as n=2. In Bii the signal in five cells (labeled i-v) indicated with coded symbols (CFA2=triangle, CFA 16=star, CFA31=arrow) to indicate copy number as follows: i) CFA 2=1, CFA 16=2, CFA 31=2. In cells ii-v the hybridization scores are ii) CFA 2=1, CFA 16=2, CFA 31=2; iii) CFA 2=1, CFA 16=0, CFA 31=1; iv) CFA 2=0, CFA 16=0, CFA 31=1; v) CFA 2=1, CFA 16=2, CFA 31=2. The mean copy number of each probe, based on these five cells, would thus be is CFA 2=2, CFA 16=1, CFA 1.6 and thus represent deletions of all three segments evaluated, indicating that the cells have a targeted copy number profile that is 1) inconsistent with the cells being derived a lymphoma, and 2) consistent with the cells being derived from an histiocytic neoplasm, as per the histologic diagnosis.

Figure 3:
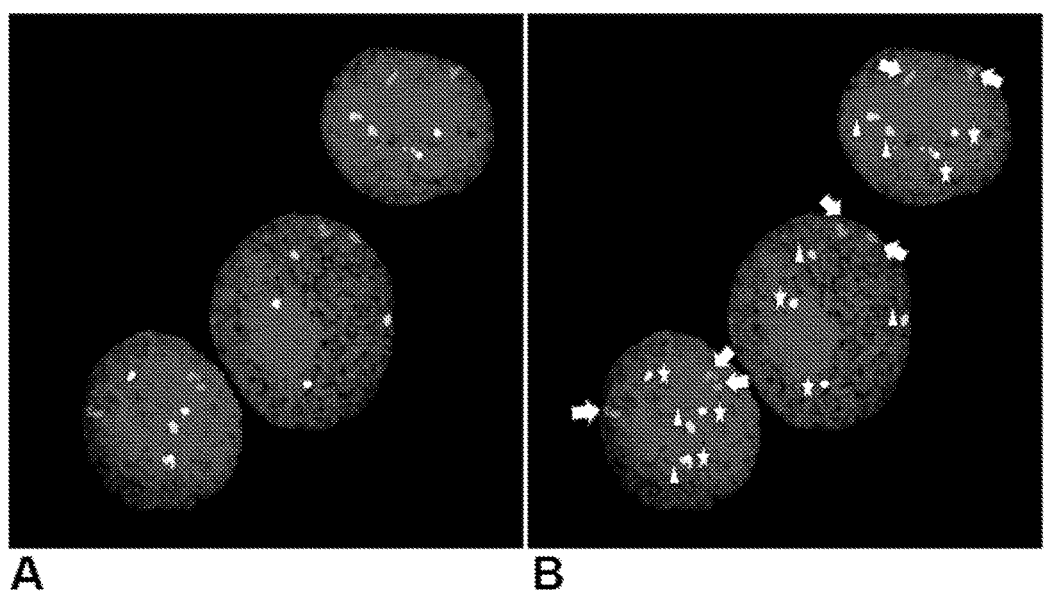

FIG. 3. Analysis of DNA copy number data indicated that segments 1, 3 and 4, representing regions of CFA 16, 31 and 2 respectively, are subject to recurrent copy number loss in canine histiocytic malignancies, but not in canine lymphoma. Here an example is shown of the three probes CFA 2 (segment 4, denoted by a triangle), CFA 16 (segment 1, denoted by a star) and CFA 31 (segment 3, denoted by an arrow)] used to detect and quantify their target segments of the canine genome in DAPI stained interphase nuclei from a dog with a histologically confirmed diagnosis of lymphoma. Panel A shows the raw data and panel B includes symbols adjacent to each signal (CFA 2=triangle, CFA 16=star, CFA 31=arrow) to indicate the signals enumerated.

In each case the copy number of the probe representing CFA 2 (triangle) is are present as two copies (n=2), while in the lower of the three cells the probes representing CFA 16 (star) and 31 (arrow) are both present as three copies (n=3). These data are consistent with the cells being derived from a lymphoma and not a histiocytic neoplasm.

The recurrent decrease in copy number of these three regions of the dog genome in histiocytic malignancies, coinciding with a recurrent gain of the same regions in canine lymphoma allows detection and enumeration of these regions to provide a discriminatory assay between the two malignancies.

Figure 4:
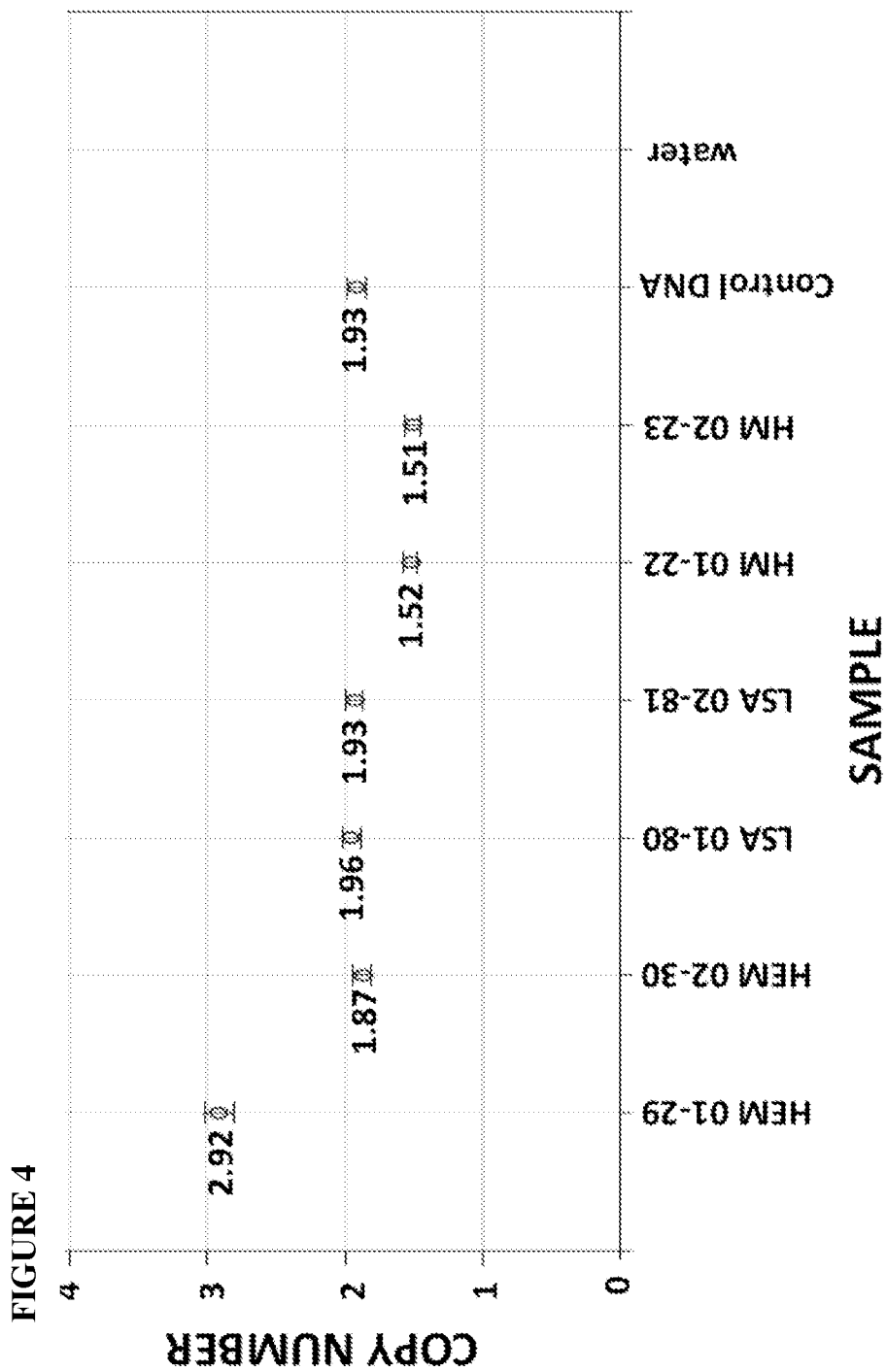

FIG. 4. Droplet digital PCR based copy number results of a CFA 31 locus for DNA samples isolated from tumor tissues of two cases of confirmed hemangiosarcoma (HEM 01-29 and HEM 02-30), two cases of confirmed lymphoma (LSA 01-80 and LSA 02-81), two cases of confirmed histiocytic malignancy (HM 02-22 and 02-23). Also shown are the data for DNA isolated from tissue of a cancer free dog (control DNA) and also from a DNA/template free control (water). X-axis shows the samples and Y-axis shows the calculated copy number of the locus on CFA 31. The DNA copy number of this locus in hemangiosarcoma and lymphoma cases is either neutral (same as control DNA) or increased (greater than that of the DNA control), and in histiocytic malignancies it is generally reduced (below that of the DNA control).

Figure 5:
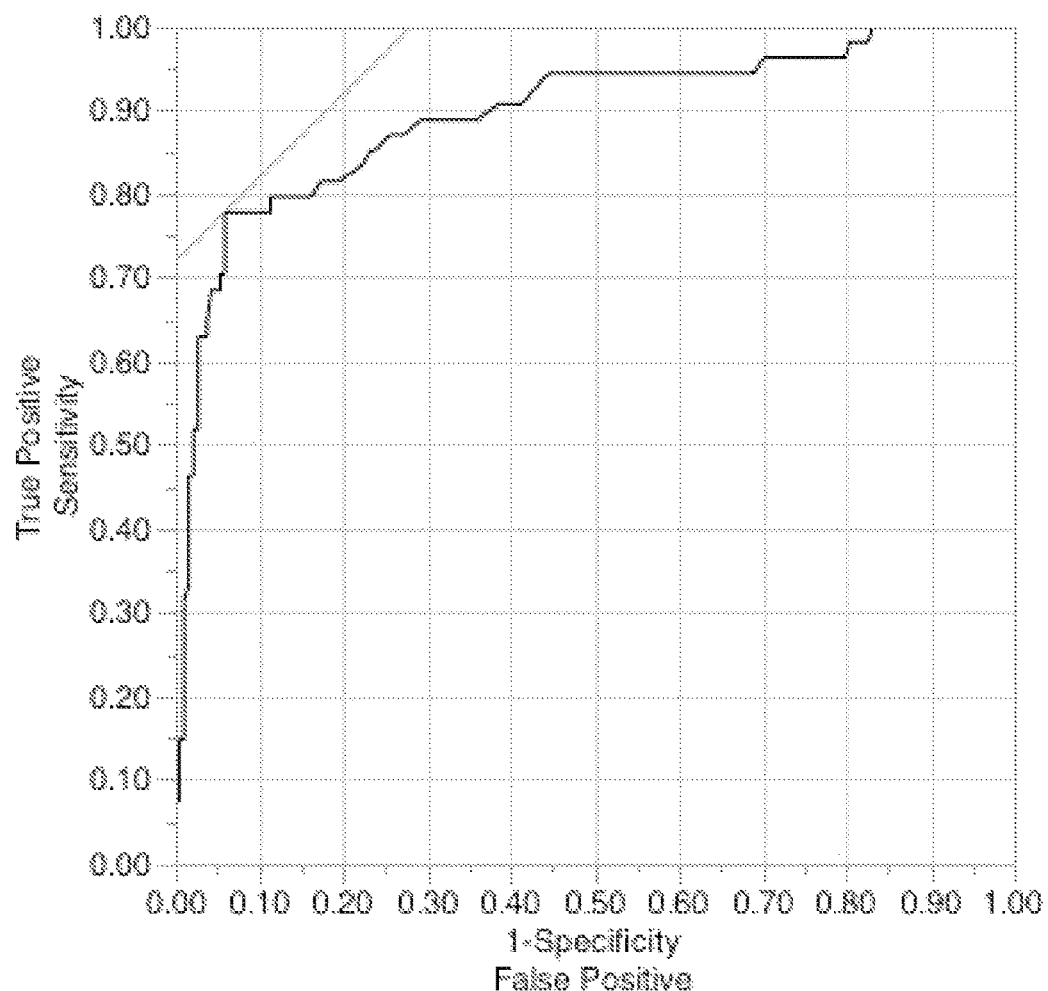

FIG. 5. Image of the Receiver Operator Curve with area under the curve of 89.5% generated using an evaluation of segment 3 alone by droplet digital PCR on 84 cases of hemangiosarcoma, 54 cases of histiocytic malignancy, and 100 cases of lymphoma; all of which were histopathologically confirmed. These data indicate the robustness of a copy number assay based on segment 3 alone via this platform, and demonstrate a reduction to practice of this assay based on the digital droplet PCR assay for discrimination of histiocytic malignancy from both lymphoma and hemangiosarcoma.

5. DETAILED DESCRIPTION OF THE INVENTION

5.1. Definitions

"Histiocytic malignancies" represent a spectrum of cancers. Histiocytic sarcomas are generally invasive (destroy the normal surrounding tissues) tumors that have a high rate of metastasis (spread to other areas of the body). Histiocytic sarcoma that is restricted to one site of the body (localized histiocytic sarcoma) is generally found in the spleen, lymph nodes, bone marrow, skin, lung, brain, or limb joints. When histiocytic sarcoma is found at more than one anatomical site, the diagnosis becomes disseminated histiocytic sarcoma, or malignant histiocytosis, both of which are cancers that progress rapidly and generally involve multiple organs simultaneously.

"Lymphoma" is a cancer caused by proliferation of lymphocytes, which are cells whose normal function is in the immune system. Dogs presenting with lymphoma have variability in site(s) of involvement because the lymphocytes are located in numerous organs of the body. The most common presentation of canine lymphoma is an enlargement of one or more lymph nodes, which may be visible and/or palpated at the surface of the body. Lymphoma may also affect organs including spleen, liver and skin, as well as the bone marrow, nervous system and gastrointestinal tract.

"Hemangiosarcoma" is a cancer that begins in the cells that line blood vessels. These tumors are mainly located in the spleen, heart, or liver, although they can also been found in other regions of the body. Hemangiosarcoma is an indolent disease, but is almost always malignant. Since the cancer tends to develop slowly, but then spreads rapidly, affected dogs can remain without clinical signs until the tumors have metastasized and/or ruptured. Once ruptured, the resulting internal bleeding can cause acute shock and death.

"Copy number" is a measurement of DNA, whether of a single locus, one or more loci, or an entire genome. In all mammals (including the domestic dog) there are two types of cells, gametes (egg and sperm cells) and somatic cells. The "wild-type", or expected/normal copy number of each locus in the genome is expected to be one (n=1) in all gametes and two (n=2) in all somatic cells of females. In male cells all autosomes (non-sex chromosomes) in every somatic cell have a wild-type copy number of n=2, but for the sex chromosomes (X and Y) each is present as one copy. A "copy number" of other than two in a somatic cell of a dog (except for sex chromosomes in males) deviates from wild-type. Such deviations include 'gains', i.e., small increases in copy numbers (n>2), 'amplifications', i.e. large increases in copy number, (generally n>5) and 'losses', i.e., decreases in copy numbers to n=1 or n=0.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling.

The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

"Probe," in the context of the present disclosure may be a collection of nucleic acid sequences, generally an oligonucleotide or polynucleotide, that can selectively hybridize to at least a portion of a target sequence under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications such as PCR, whereas a length of about 50 to about $1 \times 10^6$ nucleotides can be preferred for chromosomal probes and a length of about 5,000 to about 800,000 nucleotides or more preferably about 100,000 to about 400,000 for BAC probes. Probe may also refer to the use of a short oligonucleotide that may contain a reporter molecule, such as but not limited to TaqMan® probe, capable of being used to detecting and quantify the abundance of an amplicon.

The invention encompasses fragments of nucleic acids that can serve (1) as probes for detecting segments of domestic dog (*Canis familairis*, CFA) genome referred to as chromosomes 2, 16 and 31 (hereafter referred to as CFA 2, CFA 16 and CFA 31). The dog genome has been sequenced and is available for example, the NCBI *Canis lupus familiaris* genome database; ENSEMBL database CanFam3.1 (GCA_000002285.2) or the UCSC Genome Browser for the Dog genome, Assembly: May 2005 (Broad/canFam2) or September 2011 (Broad CanFam3.1/camFam3). See also, Lindblad-Toh et al. 2005 "Genome sequence, comparative analysis and haplotype structure of the domestic dog" *Nature* 438 (7069), 803-819.

The changes in copy number of loci located on any chromosome, including but not limited to CFA 2, 16 and 31, may be detected by a number of methods well known in the art, e.g. Southern and northern blotting, dot blotting, colony hybridizations, hybridization to an array, comparative genomic hybridization (CGH), fluorescence in situ hybridization, etc. or (2) by a method using the polymerase chain reaction (PCR), including, but not limited to the use of short oligonucleotides as primers, each of which are generally 15-30 bases in length and used to generate amplicons from CFA 2, 16 and 31, for which the quantity or absolute amount of each may be determined, for example by comparison to the amount of an amplicon generated from a stable/copy number neutral/balanced region of the genome (where copy number per cell is n=2), as a means to calculate any deviation from a copy number of n=2 in the nucleic acid sample being evaluated. An example of this would be the use of quantitative PCR or droplet digital PCR. In these examples, an additional oligonucleotide may be included to represent a "probe", such as, but not limited to, for example TaqMan® MGB assays suitable for use in DNA copy number analysis. PCR primers can comprise, in addition to CFA 2, 16 and 31 nucleic acid sequences, other sequences such as restriction enzyme cleavage sites that facilitate the use of the amplified nucleic acid. PCR is described in the following references: Saiki et al. 1988 *Science* 239 487-491; PCR Technology, Erlich, ed., Stockton Press, (1989). As explained below, PCR can be useful to detect changes in the levels of CFA 2, 16 and 31.

Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, (1989)) and *Current Protocols in Molecular Biology* (F. M. Ausubel et al., eds., John Wiley & Sons, Inc., sections 2.10 and 6.3-6.4 (1995)), the relevant portions of which are incorporated by reference herein. Moderately stringent conditions for filter hybridizations include hybridization in about 50% formamide, 6×SSC at a temperature from about 42 C to 55 C and washing at about 60 C in 0.5×SSC, 0.1% SDS. Highly stringent conditions are defined as hybridization conditions as above, but with washing at approximately 68 C in 0.2×SSC, 0.1% SDS. SSPE (1×SSPE is 0.15 M NaCl, 10 mM NaH$_2$PO$_4$, and 1.26 mM EDTA, pH 7.4) can be substituted for SSC (1×SSC is 0.15 M NaCl and 15 mM sodium citrate) in the hybridization and wash buffers; washes, optionally at least two washes, are performed for 15 minutes after hybridization is complete.

It should be understood that the wash temperature and wash salt concentration can be adjusted as necessary to achieve a desired degree of stringency by applying the basic principles that govern hybridization reactions and duplex stability, as known to those skilled in the art and described further below (see e.g., Sambrook et al., supra). When nucleic acids of known sequence are hybridized, the hybrid length can be determined by aligning the sequences of the nucleic acids (for example, using BLAST or a variant) and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (degrees C.)=2(# of A+T bases)+4(# of G+C bases). For hybrids greater than 18 base pairs in length, Tm (degrees C.)=81.5+16.6(log$_{10}$[Na+])+0.41 (% G+C)−(600 N), where N is the number of bases in the hybrid, and [Na+] is the concentration of sodium ions in the hybridization buffer. Each such hybridizing nucleic acid has a length that is at least 15 nucleotides (or at least 18 nucleotides, or at least 20, or at least 25, or at least 30, or at least 40, or at least 50, or at least 100. Sambrook et al., supra.

5.2. Polynucleotide Amplification and Determination

In many instances, it is desirable to amplify a nucleic acid sequence using any of several nucleic acid amplification procedures that are well known in the art. Specifically, nucleic acid amplification is the chemical or enzymatic synthesis of nucleic acid copies that contain a sequence complementary to a nucleic acid sequence being amplified (template). The methods and kits of the invention may use any nucleic acid amplification or detection methods known to one skilled in the art, such as those described in U.S. Pat. No. 5,525,462 (Takarada et al.); U.S. Pat. No. 6,114,117 (Hepp et al.); U.S. Pat. No. 6,127,120 (Graham et al.); U.S. Pat. No. 6,344,317 (Urnovitz); U.S. Pat. No. 6,448,001 (Oku); U.S. Pat. No. 6,528,632 (Catanzariti et al.); and PCT Pub. No. WO 2005/111209 (Nakajima et al.); all of which are incorporated herein by reference in their entirety.

Commonly used methods known in the art for the quantification of mRNA expression in a sample include northern blotting and in situ hybridization (Parker and Barnes, *Methods Mol. Biol.* 106:247-83, 1999), RNAse protection assays (Hod, *Biotechniques* 13:852-54, 1992), PCR-based methods, such as reverse transcription PCR (RT-PCR) (Weis et al., TIG 8:263-64, 1992), and array-based methods (Schena et al., *Science* 270:467-70, 1995). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE), bead-based technologies, single molecule fluorescence in situ hybridization (smFISH) studies, and gene expression analysis by massively parallel signature sequencing. Velculescu et al. 1995 *Science* 270 484-487; Streefkerk et al., 1976, *Pro Biol Fluid Proc Coll* 24 811-814; U.S. Pat. No. 5,028,545 (Soini); smFISH, Lyubimova et al. 2013 *Nat Protocol* 8(9) 1743-1758.

In some embodiments, the nucleic acids are amplified by PCR amplification using methodologies known to one skilled in the art. One skilled in the art will recognize, however, that amplification can be accomplished by any known method, such as ligase chain reaction (LCR), Qβ-replicase amplification, rolling circle amplification, transcription amplification, self-sustained sequence replication, nucleic acid sequence-based amplification (NASBA), each of which provides sufficient amplification. Branched-DNA technology may also be used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, *Adv. Clin. Chem.* 33:201-235).

The PCR process is well known in the art and is thus not described in detail herein. For a review of PCR methods and protocols, see, e.g., Innis et al., eds., *PCR Protocols, A Guide to Methods and Application*, Academic Press, Inc., San Diego, Calif. 1990; U.S. Pat. No. 4,683,202 (Mullis); which are incorporated herein by reference in their entirety. PCR reagents and protocols are also available from commercial vendors, such as Roche Molecular Systems. PCR may be carried out as an automated process with a thermostable enzyme. In this process, the temperature of the reaction mixture is cycled through a denaturing region, a primer annealing region, and an extension reaction region automatically. Machines specifically adapted for this purpose are commercially available.

5.3. High Throughput, Single Molecule Sequencing, and Direct Detection Technologies Suitable next generation sequencing technologies are widely available. Examples include the 454 Life Sciences platform (Roche, Branford, Conn.) (Margulies et al. 2005 *Nature*, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., 2006, *Genome Res.* 16, 383-393; U.S. Pat. Nos. 6,306,597 and 7,598,035 (Macevicz); U.S. Pat. No. 7,232,656 (Balasubramanian et al.)); or DNA Sequencing by Ligation, SOLiD System (Applied Biosystems/Life Technologies; U.S. Pat. Nos. 6,797,470, 7,083,917, 7,166, 434, 7,320,865, 7,332,285, 7,364,858, and 7,429,453 (Barany et al.); or the Helicos True Single Molecule DNA sequencing technology (Harris et al., 2008 *Science*, 320, 106-109; U.S. Pat. Nos. 7,037,687 and 7,645,596 (Williams et al.); U.S. Pat. No. 7,169,560 (Lapidus et al.); U.S. Pat. No. 7,769,400 (Harris)), the single molecule, real-time (SMRT™) technology of Pacific Biosciences, and sequencing (Soni and Meller, 2007, *Clin. Chem.* 53, 1996-2001) which are incorporated herein by reference in their entirety. These systems allow the sequencing of many nucleic acid molecules isolated from a specimen at high orders of multiplexing in a parallel fashion (Dear, 2003, *Brief Funct. Genomic Proteomic*, 1(4), 397-416 and McCaughan and Dear, 2010, *J. Pathol.*, 220, 297-306). Each of these platforms allow for sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Nucleic acids may be immobilized to a solid support, hybridized with a sequencing primer, incubated with DNA polymerase, ATP sulfurylase, luciferase, apyrase, adenosine 5' phosphosulfate and luciferin. Nucleotide solutions are sequentially added and removed. Correct incorporation of a nucleotide releases a pyrophosphate, which interacts with ATP sulfurylase and produces ATP in the presence of adenosine 5' phosphosulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, *Nat. Prot.* 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., 2003, *J. Biotech.* 102, 117-124). Such a system can be used to exponentially amplify amplification products generated by a process described herein, e.g., by ligating a heterologous nucleic acid to the first amplification product generated by a process described herein.

Certain single-molecule sequencing aspects are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET-based single-molecule sequencing or detection, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each other for energy transfer to occur successfully. Bailey et al. recently reported a highly sensitive (15 pg methylated DNA) method using quantum dots to detect methylation status using fluorescence resonance energy transfer (MS-qFRET)(Bailey et al. 2009, *Genome Res.* 19(8), 1455-1461, which is incorporated herein by reference in its entirety).

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., Braslavsky et al., PNAS 100(7): 3960-3964 (2003); U.S. Pat. No. 7,297,518 (Quake et al.) which are incorporated herein by reference in their entirety). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer-released linear amplification product complexes with the immobilized capture sequences, immobilizes released linear amplification products to solid supports for single pair FRET-based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step (a) with a different fluorescently labeled nucleotide.

The technology may be practiced with digital PCR. Digital PCR was developed by Kalinina and colleagues (Kalinina et al., 1997, *Nucleic Acids Res.* 25; 1999-2004) and further developed by Vogelstein and Kinzler (1999, *Proc. Natl. Acad. Sci. U.S.A.* 96; 9236-9241). The application of digital PCR is described by Cantor et al. (PCT Pub. Nos. WO 2005/023091A2 (Cantor et al.); WO 2007/092473 A2, (Quake et al.)), which are hereby incorporated by reference in their entirety. Digital PCR takes advantage of nucleic acid (DNA, cDNA or RNA) amplification on a single molecule level, and offers a highly sensitive method for quantifying low copy number nucleic acids. Fluidigm® Corporation, BioRad's Digital PCR and Raindance technologies all offer systems for the digital analysis of nucleic acids. See, Karlin-Neumann G et al. (2012). Probing copy number variations using Bio-Rad's QX100™ Droplet Digital™ PCR system. Bio-Rad Bulletin 6277; Diderot et al., *Clinical Chemistry* February 2013 clinchem.2012.193409.

In some embodiments, nucleotide sequencing may be by solid phase single nucleotide sequencing methods and processes. Solid phase single nucleotide sequencing methods involve contacting sample nucleic acids and a solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in PCT Pub. No. WO 2009/091934 (Cantor).

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors; and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected.

A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

Next generation sequencing techniques may be applied to measure expression levels or count numbers of transcripts using RNA-seq or whole transcriptome shotgun sequencing. See, e.g., Mortazavi et al. 2008 *Nat Meth* 5(7) 621-627; or Wang et al. 2009 *Nat Rev Genet* 10(1) 57-63.

Nucleic acids in the invention may be counted using methods known in the art. In one embodiment, NanoString's nCounter system may be used. Geiss et al. 2008 *Nat Biotech* 26(3) 317-325; U.S. Pat. No. 7,473,767 (Dimitrov). Alternatively, Fluidigm's Dynamic Array system may be used. Byrne et al. 2009 *PLoS ONE* 4 e7118; Helzer et al. 2009 *Can Res* 69 7860-7866. For reviews, see also Zhao et al. 2011 *Sci China Chem* 54(8) 1185-1201; and Ozsolak and Milos 2011 *Nat Rev Genet* 12 87-98.

The invention encompasses any method known in the art for enhancing the sensitivity of the detectable signal in such assays, including, but not limited to, the use of cyclic probe technology (Bakkaoui et al., 1996, *BioTechniques* 20: 240-8, which is incorporated herein by reference in its entirety); and the use of branched probes (Urdea et al., 1993, *Clin. Chem.* 39, 725-6; which is incorporated herein by reference in its entirety). The hybridization complexes are detected according to well-known techniques in the art.

Reverse transcribed or amplified nucleic acids may be modified nucleic acids. Modified nucleic acids can include nucleotide analogs, and in certain embodiments include a detectable label and/or a capture agent. Examples of detectable labels include, without limitation, fluorophores, radioisotopes, colorimetric agents, light emitting agents, chemiluminescent agents, light scattering agents, enzymes and the like. Examples of capture agents include, without limitation, an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments.

The invention described herein may be used in conjunction with other molecular techniques for detection of cancer such as US Pat Pub 2013/0171637 (Giafis et al.) the contents of which are hereby incorporated by reference in its entirety.

5.4. Statistical Methods

The data may be ranked for its ability to distinguish biomarkers in both the 1 versus all (i.e., disease versus normal) and the all-pairwise (i.e., normal versus specific disease) cases. One statistic used for the ranking is the area under the receiver operator characteristic (ROC) curve (a plot of sensitivity versus (1-specificity)). Although biomarkers are evaluated for reliability across datasets, the independent sample sets are not combined for the purposes of the ROC ranking. As a result, multiple independent analyses are performed and multiple independent rankings are obtained for each biomarker's ability to distinguish groups of interest.

It is to be understood that other genes and/or diagnostic criteria may be used in this invention. For example, animal signs, standard blood workups, the results of imaging tests, and/or histological evaluation may optionally be combined with biomarkers disclosed herein.

Such analysis methods may be used to form a predictive model, and then use that model to classify test data. For example, one convenient and particularly effective method of classification employs multivariate statistical analysis modeling, first to form a model (a "predictive mathematical model") using data ("modeling data") from samples of known class (e.g., from subjects known to have, or not have, a particular class, subclass or grade of lung cancer), and second to classify an unknown sample (e.g., "test data"), according to lung cancer status.

Pattern recognition (PR) methods have been used widely to characterize many different types of problems ranging for example over linguistics, fingerprinting, chemistry and psychology. In the context of the methods described herein, pattern recognition is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots that can be interpreted by the human eye. The other approach is termed "supervised" whereby a training set of samples with known class or outcome is used to produce a mathematical model and is then evaluated with independent validation data sets.

Unsupervised PR methods are used to analyze data without reference to any other independent knowledge. Examples of unsupervised pattern recognition methods include principal component analysis (PCA), hierarchical cluster analysis (HCA), and non-linear mapping (NLM).

Alternatively, and in order to develop automatic classification methods, it has proved efficient to use a "supervised" approach to data analysis. Here, a "training set" of biomarker data is used to construct a statistical model that predicts correctly the "class" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each class, for example, each class of lung cancer in terms of its biomarker expression profile. It is also possible to obtain confidence limits on any predictions, for example, a level of probability to be placed on the goodness of fit (see, for example, Sharaf; Illman; Kowalski, eds. (1986). Chemometrics. New York: Wiley). The robustness of the predictive models can also be checked using cross-validation, by leaving out selected samples from the analysis.

Examples of supervised pattern recognition methods include the following nearest centroid methods (Dabney 2005 *Bioinformatics* 21(22):4148-4154 and Tibshirani et al. 2002 *Proc. Natl. Acad. Sci. USA* 99(10):6576-6572); soft independent modeling of class analysis (SIMCA) (see, for example, Wold, (1977) Chemometrics: theory and application 52: 243-282.); partial least squares analysis (PLS) (see, for example, Wold (1966) Multivariate analysis 1: 391-420; Joreskog (1982) Causality, structure, prediction 1: 263-270); linear discriminant analysis (LDA) (see, for example, Nillson (1965). Learning machines. New York.); K-nearest neighbor analysis (KNN) (see, for example, Brown and Martin 1996 *J Chem Info Computer Sci* 36(3):572-584); artificial neural networks (ANN) (see, for example, Wasserman (1993). *Advanced methods in neural computing*. John Wiley & Sons, Inc; O'Hare & Jennings (Eds.). (1996). Foundations of distributed artificial intelligence (Vol. 9). Wiley); probabilistic neural networks (PNNs) (see, for example, Bishop & Nasrabadi (2006). Pattern recognition and machine learning (Vol. 1, p. 740). New York: Springer; Specht, (1990). Probabilistic neural networks. Neural networks, 3(1), 109-118); rule induction (RI) (see, for example, Quinlan (1986) Machine learning, 1(1), 81-106); and, Bayesian methods (see, for example, Bretthorst (1990). An introduction to parameter estimation using Bayesian probability theory. In Maximum entropy and Bayesian methods (*pp.* 53-79). Springer Netherlands; Bretthorst, G. L. (1988). Bayesian spectrum analysis and parameter estimation (Vol. 48). New York: Springer-Verlag); unsupervised hierarchical clustering (see for example Herrero 2001 *Bioinformatics* 17(2) 126-136). In one embodiment, the classifier is the centroid based method described in Mullins et al. 2007 *Clin Chem* 53(7):1273-9, which is herein incorporated by reference in its entirety for its teachings regarding disease classification.

It is often useful to pre-process data, for example, by addressing missing data, translation, scaling, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may replaced or "filled" with, for example, the mean value of a column ("mean fill"); a random value ("random fill"); or a value based on a principal component analysis ("principal component fill"). Each of these different approaches will have a different effect on subsequent PR analysis.

"Translation" of the descriptor coordinate axes can be useful. Examples of such translation include normalization and mean centering. "Normalization" may be used to remove sample-to-sample variation. Many normalization approaches are possible, and they can often be applied at any of several points in the analysis. "Mean centering" may be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt (StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centred and unit variance scaled. This technique is a very useful because each descriptor is then weighted equally and large and small values are treated with equal emphasis. This can be important for analytes present at very low, but still detectable, levels.

Several supervised methods of scaling data are also known. Some of these can provide a measure of the ability of a parameter (e.g., a descriptor) to discriminate between classes, and can be used to improve classification by stretching a separation. For example, in "variance weighting," the variance weight of a single parameter (e.g., a descriptor) is calculated as the ratio of the inter-class variances to the sum of the intra-class variances. A large value means that this variable is discriminating between the classes. For example, if the samples are known to fall into two classes (e.g., a training set), it is possible to examine the mean and variance of each descriptor. If a descriptor has very different mean values and a small variance, then it will be good at separating the classes. "Feature weighting" is a more general description of variance weighting, where not only the mean and standard deviation of each descriptor is calculated, but other well-known weighting factors, such as the Fisher weight, are used.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The process of comparing a measured value and a reference value can be carried out in any convenient manner appropriate to the type of measured value and reference value for the discriminative gene at issue. "Measuring" can be performed using quantitative or qualitative measurement techniques, and the mode of comparing a measured value and a reference value can vary depending on the measurement technology employed. For example, when a qualitative colorimetric assay is used to measure expression levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values. In other examples, measured values are qualitative. As with qualitative measurements, the comparison can be made by inspecting the numerical data, or by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker. Alternately, a separate device (e.g., a digital computer) may be used to compare the measured value(s) and the reference value(s). Automated devices for comparison may include stored reference values for the biomarker being measured, or they may compare the measured value(s) with reference values that are derived from contemporaneously measured reference samples (e.g., samples from control subjects).

As will be apparent to those of skill in the art, when replicate measurements are taken, the measured value that is compared with the reference value is a value that takes into account the replicate measurements. The replicate measurements may be taken into account by using either the mean or median of the measured values as the "measured value."

The invention also includes methods of identifying animals for particular treatments or selecting animals for which a particular treatment would be desirable or contraindicated.

The methods above may be performed by a reference laboratory, a veterinary hospital pathology laboratory, a university veterinary laboratory, a veterinarian's office or a veterinarian. The methods above may further comprise an algorithm and/or statistical analysis.

5.5. Samples

The sample may be a blood, saliva, stool, tissue, or urine sample provided the sample contains cells of the neoplasm. Preferably the cell or cells will be obtained directly from a suspected neoplastic mass, including but not limited to lymph nodes. For the cytogenetic assays, as shown in the examples, cells are used to provide templates for the FISH probes. For PCR assays, tumor DNA may be obtained from cells or a nucleic acid extraction from cells. The sample may be obtained from any collection of tissues, or bodily fluids containing cells in which biomarker(s) can be detected. Examples of such samples include, but are not limited to, biopsies and smears. Bodily fluids useful in the present invention include blood, lymph, urine, saliva, nipple aspirates, gynecological fluids, or any other bodily secretion or derivative thereof. Blood can include whole blood, plasma, serum, or any derivative of blood containing cells. Body samples may be obtained from a patient by a variety of techniques including, for example, by scraping or swabbing an area, by using a needle to aspirate cells or bodily fluids, or by removing a tissue sample (i.e., biopsy). In some embodiments, the sample may be obtained from a tissue from a biopsy, such as a wedge, needle biopsy or excisional biopsy. Methods for collecting various body samples are well known in the art. Fixative and staining solutions may be applied to the cells or tissues for preserving the specimen and for facilitating examination. Samples, particularly tumor tissue samples, may be transferred to a glass slide for viewing under magnification. In one embodiment, the body sample is a formalin-fixed, paraffin-embedded (FFPE) tissue sample.

5.6. Compositions and Kits

The invention provides compositions and kits for distinguishing histiocytic malignancy from lymphoma in a dog comprising: (a) at least one reagent selected from the group consisting of: a plurality of nucleic acid probes capable of specifically detecting CFA 2, CFA 16 and CFA 31; and (b) instructions for use in measuring a copy number of CFA 2, CFA 16 and CFA 31 in a biological sample from a dog wherein if the copy number of CFA 2 and/or CFA 16 and/or CFA 31 in cells from the dog sample are <2 determining the dog has an increased likelihood of having a histiocytic malignancy rather than a lymphoma or hemangiosarcoma.

The instructions comprise determining in a sample of relevant cells obtained from the dog the presence of chromosomal abnormalities, wherein the presence of chromosomal abnormalities involving at least two of the probes indicates that the patient has a particular cancer. Such kits may further comprise, or consist of, blocking agents or other probes, various labels or labeling agents to facilitate detection of the probes, reagents for hybridization (e.g., buffers), a metaphase spread, and the like.

Unless defined otherwise, all technical and scientific terms used herein have the same meaning as commonly understood by one of ordinary skill in the art to which this invention belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The following Examples further illustrate the invention and are not intended to limit the scope of the invention. In particular, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

6. EXAMPLES

6.1. Experimental Data

Tumor biopsy samples were obtained from 101 dogs with a confirmed diagnosis of lymphoma, and 44 dogs with a confirmed diagnosis of a histiocytic neoplasm. Genomic DNA was isolated from all 145 tumor biopsies and each was used to generate a genome wide DNA copy profile, using a comparative genomic hybridization array comprising 180,000 unique 60-mer oligonucleotide probes at ~13.5 kb mean spacing throughout the canine genome (ID#25522, Agilent Technologies). All procedures used to generate these data have been reported previously by the inventor's laboratory (Thomas et al., 2011, Hedan et al., 2011, Angstadt et al., 2012).

Following hybridization, each array was scanned at 3 µm resolution using an Agilent G2565CA DNA Microarray Scanner with SureScan High resolution technology (Agilent Technologies). Scan data were assessed for data quality by the 'Quality Metrics' report in Agilent's Feature extraction software (v10.5)(Agilent Technologies). FASST2 Segmentation Algorithm, a Hidden Markov Model (HMM) based approach, was used to make copy number calls. The FASST2 algorithm, unlike other common HMM methods for copy number estimation, does not aim to estimate the copy number state at each probe but uses many states to cover more possibilities, such as mosaic events. These state values are then used to make calls based on a log-ratio threshold. The significance threshold for segmentation was set at $5 \times 10^{-6}$, also requiring a minimum of three probes per segment and a maximum probe spacing of 1 Mb between adjacent probes before breaking a segment. The log ratio thresholds for single copy gain and single copy loss were set at +0.2 and −0.23, respectively.

DNA copy number aberrations 'called' by the FASST2 segmentation algorithm were compared across the cohorts of histiocytic malignancies (group A) and lymphoma (group B) to identify those that had significantly different frequencies between the cancer types. The full lengths of chromosomes 2, 16 and 31 were the top three chromosomes to show differential copy number status when comparing canine histiocytic malignancies with canine lymphoma. Chromosomes were segmented to identify subchromosomal regions that were highly significantly different in terms of frequency of an aberration in group A vs. group B, and had to meet a minimum p-value of $1\times10^{-10}$, based on a two-tailed Fisher's Exact test, as well as a minimum of 55% difference in frequencies between the two groups. The five FASSTT2 segmented regions with the greatest significant differences between the two cancer types are shown in Table 1.

Third, the sensitivity and specificity were calculated. Sensitivity measures the proportion of actual positives that are correctly identified as such (in this case the percentage of HM dogs who are correctly identified as being HM). Specificity measures the proportion of negatives, which are correctly identified (in this case the percentage of LSA dogs who are correctly identified as being LSA).

Fourth, an overall misclassification rate was calculated. This measure tells the percentage of dogs that are

TABLE 1

Top five FASST2 segmented regions of the canine genome that show significant differences in copy number aberration in canine lymphoma (LSA) and histiocytic malignancies (HM). Each region represented a high frequency copy number loss (deletion), in HM cases that was minimally present or absent in LSA cases. Each region is defined by the start and stop base pair position in the canine genome assembly CanFam2. Segments 1, 3 and 4 (bold text) are each >200 Kb and so of a size suited to detection and quantification by gold standard fluorescence in situ hybridization (FISH) analysis. Regions 2 and 5 are also discriminatory and would be amenable to use in oligonucleotide based FISH that require smaller probe sizes. All five regions would be amenable to detection and quantification using PCR methods to detect and quantify their mean copy number in cell population.

| Segment | Region (chromosome: bp) | Region Length (bp) | Freq. of loss in HM (%) | Freq. of loss in LSA (%) | Difference | p-value | q-bound |
|---|---|---|---|---|---|---|---|
| 1 | chr16: 31,674,246-32,429,051 | 754805 | 93.2 | 7.9 | 85.3 | 2.02E−24 | 5.28E−21 |
| 2 | chr31: 30,613,619-30,702,648 | 89029 | 75.0 | 0.0 | 75.0 | 1.63E−23 | 1.79E−20 |
| 3 | chr31: 33,346,317-33,709,291 | 362974 | 72.7 | 0.0 | 72.7 | 1.54E−22 | 5.92E−20 |
| 4 | chr2: 31,017,808-31,586,959 | 569151 | 59.1 | 0.0 | 59.1 | 2.88E−17 | 9.36E−16 |
| 5 | chr30: 42,742,706-42,761,671 | 18965 | 68.2 | 0.0 | 68.2 | 1.11E−20 | 1.10E−18 |

Statistical Analysis.

Using the frequencies provided for the deletions in HM and LSA tissues, the measures of association and potential predictive performance were calculated for the three largest of the top five regions (i.e. segments 1, 3 and 4). These three regions were selected from the top five shown in Table 1 on the basis of their size being >200 kb in length, which allows copy number to be detected and enumerated using single locus probe fluorescence in situ hybridization (FISH) analysis using genomic clones such as bacteria artificial chromosomes (BACs).

Several statistical measures were calculated.

First, the relative risk was calculated. As calculated, the risk ratio can be interpreted as the overall risk of a dog being a HM given that it has a copy number loss, compared to the overall risk that a dog is a LSA given that it has a copy number loss. Relative risk (RR) is simply the probability or relationship between two events. For example, a relative risk of 10 would indicate that a dog with the aberration would be ten times more likely to be a HM than a LSA.

Second, the odds ratio was calculated. As calculated, the odds ratio can be interpreted as the odds of a dog being a HM given that it has a copy number loss compared to the odds that a dog is a LSA given that it has a copy number loss. Instead of using pure percentages (like in RR), OR uses the ratio of odds. The OR explains the 'odds' not in its colloquial definition (i.e. chance) but rather on its statistical definition, which is the probability of an event over (divided by) the probability of a certain event not happening.

misclassified by this marker. The accuracy of the test overall would simply be one minus (1−) the misclassification rate.

Additionally, 95% confidence intervals were calculated for each of these measures for each region.

The statistical findings and their interpretations are presented for each of the three regions individually in tables 2, 3 and 4

TABLE 2

Statistical information regarding copy number decrease of Segment 1: chr16: 31,674,246-32,429,051 when comparing cells from HM to those from LSA

| Measure | Value | 95% Confidence Interval | |
|---|---|---|---|
| Relative Risk | 26.776 | 9.717 | 100.613 |
| Odds Ratio | 158.875 | 35.494 | 836.730 |
| Sensitivity | 0.932 | 0.832 | 0.981 |
| Specificity | 0.921 | 0.877 | 0.942 |
| Misclassification Rate | 0.076 | 0.046 | 0.136 |

TABLE 3

Statistical information regarding copy number decrease of Segment 3: chr31: 33,346,317-33,709,291 when comparing cells from HM to those from LSA

| Measure | Value | 95% Confidence Interval | |
|---|---|---|---|
| Relative Risk | 9.417 | 6.383 | 9.417 |
| Odds Ratio | Infinite | 47.901 | Infinite |
| Sensitivity | 0.727 | 0.644 | 0.727 |
| Specificity | 1.00 | 0.964 | 1.00 |
| Misclassification Rate | 0.083 | 0.083 | 0.133 |

TABLE 4

Statistical information regarding copy number decrease of Segment 4: chr2: 31,017,808-31,586,959 when comparing cells from HM to those from LSA

| Measure | Value | 95% Confidence Interval | |
|---|---|---|---|
| Relative Risk | 6.611 | 4.694 | 6.611 |
| Odds Ratio | Infinite | 26.795 | Infinite |
| Sensitivity | 0.591 | 0.506 | 0.591 |
| Specificity | 1.00 | 0.963 | 1.00 |
| Misclassification Rate | 0.124 | 0.124 | 0.175 |

Combinatorial Analysis.

To evaluate the potential predictive power of a multivariate model (using up to all three regions together, with gain and loss information for all three regions included), a decision tree model was constructed using the J48 algorithm (Ross Quinlan (1993). C4.5: Programs for Machine Learning. Morgan Kaufmann Publishers, San Mateo, Calif.) and the resulting tree shown below.

CFA16=0.0: LSA (93.0/2.0)

CFA16=−

|CFA31=−: HS/MH (27.0)

|CFA31=0.0

||CFA2=0.0: LSA (5.0/1.0)

||CFA2=−: HS/MH (6.0)

||CFA2=+: HS/MH (0.0)

||CFA2=CFA2: HS/MH (0.0)

|CFA31=+

||CFA2=0.0: LSA (5.0/1.0)

||CFA2=−: HS/MH (3.0)

||CFA2=+: HS/MH (0.0)

||CFA2=CFA2: HS/MH (0.0)

|CFA31=CFA31: HS/MH (0.0)

CFA16=CFA16: LSA (0.0)

CFA16=+: LSA (2.0)

As predicted, combining two or more of the segments, in decreasing order of individual significance, serves to increase the power of this model to separate these two cancer types, as shown in the table 5

TABLE 5

Summary of statistical significance of an assay when using a combinatorial approach of the three key genomic segments 1, 3 and 4.

| | Segment(s) evaluated | | |
|---|---|---|---|
| | Segment 1 only | Segments 1 + 3 | Segments 1 + 3 + 4 |
| Sensitivity | 0.932 | 0.929 | 0.973 |
| Specificity | 0.921 | 0.936 | 0.972 |
| Area Under Curve | — | 0.936 | 0.971 |
| Misclassification Rate | 0.076 | 0.071 | 0.028 |

Detection and quantification of the discriminating segments were further evaluated to assess if the copy number of these segments was able to further distinguish between histiocytic malignancies and hemangiosarcoma. To accomplish this, DNA was isolated from 84 cases of hemangiosarcoma [histopathologically confirmed] and each was assessed for copy number of segment 3 by droplet digital PCR. Comparison to the data from histiocytic malignancies resulted in a Receiver Operator Curve of 0.865 (86.5%), with an associated specificity and sensitivity of 88.1% and 77.8% respectively for a positive diagnosis of a histiocytic malignancy.

ASPECTS OF THE DISCLOSURE

The invention is based on the evaluation of neoplastic cells obtained from canine tumor specimens to determine the copy number status of regions of the canine genome identified as segments 1, 3 and 4 above. Combining the copy number data for all three segments provides 97.3% sensitivity and 97.2% specificity to distinguish between a canine histiocytic neoplasm and a canine lymphoma. Assessment of copy number status of region 3 alone in histiocytic malignancies and hemangiosarcoma provides sensitivity and specificity of 88.1% and 77.8%, respectively for a positive diagnosis of a histiocytic malignancy, while assessment of the copy number status of region 3 alone in all three diseases provides and area under the Receiver Operator Curve of 0.894 (89.4%), a 94% specificity and 77.8% sensitivity for a positive diagnosis of a histiocytic malignancy. Detection and quantification of the copy number status of one or more of these segments may be performed by a variety of laboratory based approaches including, but not limited to, fluorescence in situ hybridization (FISH), comparative genomic hybridization, quantitative PCR, digital PCR and next generation sequencing read depth.

The gold standard assay for detecting and quantifying DNA copy number changes in cells currently is by fluorescence in situ hybridization (FISH) analysis. To demonstrate the practical means by which the invention may be used to assess individual patients, we have used FISH analysis with single locus probes (individually or forming a contig) designed to detect and quantify the three informative segments of the canine genome located described above, representing regions of CFA 16, 31 and 2.

The following examples serve to illustrate the present invention and are not intended to limit the scope of the claimed invention in any way.

FISH analysis may be performed using any single locus probe, or probe pools, that will allow detection and quantification of each region being evaluated. Such probes may comprise, but are not limited to, one or more clones of genomic DNA segments within the target region, or pools of oligonucleotides within the target regions. Regardless of probe composition, each may be labeled with a hapten (e.g., bio-x-dNTP or dig-x-dNTP) or a fluorochrome (eg Alexa-fluor-dNTP, Spectrum-fluor-dNTP), hybridized to the cells of interest using routine in situ hybridization protocols, and hybridization sites detected and enumerated using routine fluorescence microscopy with appropriate fluorescence filters and image acquisition tools and software. Assessment of individual cells provided a cell to cell comparison within the cell population being assessed and analysis of multiple cells in a patient specimen allow derivation of the mean DNA copy number of the segments in the cell population.

In this example, for the purposes of FISH analysis in cells derived from either fresh tumor tissue or fixed tumor tissue, overlapping canine BAC probes were selected for each of the three segments from the CHORI-82 BAC library https://bacpac.chori.org/library.php?id=253) as show in Table 6.

TABLE 6

Canine BAC clones from the CHORI-82 library (https://bacpac.chori.org/library.php?id=253) used to generate probes to detect and quantify three regions of the canine genome using FISH analysis of cells derived from fresh or fixed tissue specimens. The positions (in base pairs) were obtained from the CanFam2 genome assembly in the UCSC Genome browser gateway at http://genome.csdb.cn/cgi-bin/hgGateway?db=canFam2.

| Segment | CHORI82 clone | Start position | Stop position | Total size of probed region |
|---|---|---|---|---|
| 1 | 277C05 | 31683415 | 31891592 | |
| chr16: 31,674,246-32,429,051 | 287P11 | 32018044 | 32194654 | |
| | 087C13 | 32168481 | 32383135 | 699720 |
| 3 | 285I09 | 33394572 | 33589394 | |
| chr31: 33,346,317-33,709,291 | 300P10 | 33425560 | 33587018 | |
| | 308N22 | 33475117 | 33674529 | 279957 |
| 4 | 506M16 | 31246128 | 31454594 | |
| chr2: 31,017,808-31,586,959 | 509P07 | 31302995 | 31478958 | |
| | O13D24 | 31330135 | 31519839 | 273711 |

FISH of these probes to non-neoplastic (control) cells is shown in FIG. 1, FISH of the probes to cells from a case of a histiocytic neoplasm are shown in FIG. 2 and FISH of the probes to cells from a case of canine lymphoma are shown in FIG. 3.

An additional example of use of this approach is with droplet digital PCR (ddPCR), also used to detect and quantify aberrant DNA copy number. In this example a custom ddPCR assay was used to quantify region 3 (CFA 31). These data demonstrated that this approach separated histiocytic malignancies from lymphoma and hemangiosarcoma with high specificity and sensitivity (0.940 and 0.778, respectively) (FIGS. 4 and 5).

SUMMARY

These data indicate a significant difference in the DNA copy number status of three regions of the canine genome defined above when evaluated in tumor samples derived from confirmed cases of canine lymphoma, hemangiosarcoma, and histiocytic malignancies. The data provided indicate that a resulting assay for copy number status, even if just based on assessment of segment 1 (CFA 16) alone, would offer very high specificity (0.921) and sensitivity (0.931) to separate a diagnosis of lymphoma from that of a histiocytic malignancy. Addition of segments 2 (CFA 31) and 4 (CFA 2) increases overall specificity and sensitivity to 0.972 and 0.973, respectively in the comparison of lymphoma to histiocytic malignancy. Further, the evaluation of segment 3 (CFA 31) alone, offers very high specificity (0.940) and high sensitivity (0.778) to discriminate between canine histiocytic malignancies and lymphoma and hemangiosarcoma. These numbers are higher than many assays currently available in the human testing space and indicate that any means to detect and quantify these three segments in canine cells would allow a high level of confidence in determining if the cells evaluated are from an histiocytic neoplasm or lymphoma, or hemangiosarcoma. An example of reduction to practice of such an assay was presented, using three BAC contigs as differentially labeled FISH probes, to detect and quantify copy number of all three segments in tumor cells. In addition a further example was presented using droplet digital PCR to detect and quantity copy number of region 3.

7. REFERENCES

1. Andrea Y. Angstadt, Venugopal Thayanithy, Subbaya Subramanian, Jaime F. Modiano, and Matthew Breen (2012). A genome-wide approach to comparative oncology: High-resolution oligonucleotide aCGH of canine and human OS pinpoints shared microaberrations. Cancer Genetics. 205(11):572-587
2. Benoit Hedan, Rachael Thomas, Alison Motsinger-Reif, Jérôme Abadie, Catherine André, John Cullen and Matthew Breen (2011). Molecular cytogenetic characterization of canine histiocytic sarcoma: A spontaneous model for human histiocytic cancer identifies deletion of tumor suppressor genes and highlights influence of genetic background on tumor behavior. BMC Cancer 2011, 11:201 doi: 10.1186/1471-2407-11-201 (published May 26, 2011)
3. Thomas, R., E. L. Seiser, A. A. Motsinger-Reif, L. Borst, V. E. Valli, K. Kelley, S. E. Suter, D. Argyle, K. Burgess, J. Bell, K. Lindblad-Toh, J. F. Modiano and M. Breen (2011). "Refining tumor-associated aneuploidy through 'genomic recoding' of recurrent DNA copy number aberrations in 150 canine non-Hodgkin's lymphomas." Leukemia and Lymphoma 52(7):1321-1335.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application were specifically and individually indicated to be incorporated by reference.

What is claimed is:

1. A method for treating a dog with lymphoma, the method comprising:
   (a) measuring copy numbers of CFA 2, CFA 16, and CFA 31 in a biological sample from a dog suspected of having lymphoma or a histiocytic malignancy, wherein:
      (i) the biological sample comprises neoplastic cells; and
      (ii) the copy numbers of CFA 2, CFA 16, and CFA 31 are measured by aberrations at CFA chr2:31,017,808-31,586,959, CFA chr16:31,674,246-32,429,051, and CFA chr31:33,346,317-33,709,291 from CamFam2, respectively;
   (b) detecting a normal or elevated copy number at CFA 2, CFA 16, and CFA 31 compared to a normal control in the biological sample;
   (c) diagnosing the dog with lymphoma; and
   (d) treating the dog with standard of care (SOC) chemotherapy using either single agent or multiagent protocols.

2. The method of claim 1, wherein the copy numbers are measured by fluorescence in situ hybridization (FISH).

3. The method of claim 1, wherein the copy numbers are measured by polymerase chain reaction (PCR).

4. The method of claim 1, wherein the copy numbers are measured by comparative genomic hybridization (CGH).

5. The method of claim 1, wherein the copy numbers are measured by next generation sequencing.

6. The method of claim 1, wherein the biological sample is a tissue sample.

7. The method of claim 1, wherein the sample is a fresh-frozen sample.

8. The method of claim 1, wherein the sample is a fresh sample.

9. The method of claim 1, wherein the sample is a formalin-fixed, paraffin-embedded sample.

10. The method of claim 1, wherein the copy numbers at CFA 2, CFA 16, and CFA 31 are measured with probes of about 15 to about $1\times10^6$ nucleotides in length.

11. The method of claim 10, wherein the copy numbers are measured with probes of about 5,000 to about 800,000 nucleotides in length.

12. The method of claim 10, wherein the copy numbers are measured with probes of about 100,000 to about 400,000 nucleotides in length.

13. A method for selecting and treating a dog suspected of having a canine lymphoma, the method comprising:
   (a) providing a dog suspected of having a lymphoma or a histiocytic malignancy;
   (b) measuring copy numbers of CFA 2, CFA 16, and CFA 31 in a biological sample from the dog, wherein:
      (i) the biological sample comprises cells obtained directly from a suspected neoplastic mass; and
      (ii) the copy numbers of CFA 2, CFA 16, and CFA 31 are measured by aberrations at CFA chr2:31,017,808-31,586,959, CFA chr16:31,674,246-32,429,051, and CFA chr31:33,346,317-33,709,291 from CamFam2, respectively;
   (b) detecting normal or elevated copy number at CFA 2, CFA 16, and CFA 31 compared to a normal control in the biological sample;
   (c) diagnosing the dog with lymphoma; and
   (d) treating the dog with standard of care (SOC) chemotherapy using either single agent or multiagent protocols.

14. The method of claim 13, wherein the copy numbers at CFA 2, CFA 16, and CFA 31 are measured with probes of about 15 to about $1\times10^6$ nucleotides in length.

15. The method of claim 14, wherein the copy numbers are measured with probes of about 5,000 to about 800,000 nucleotides in length.

16. The method of claim 14, wherein the copy numbers are measured with probes of about 100,000 to about 400,000 nucleotides in length.

* * * * *